US008859803B2

(12) United States Patent
Tani

(10) Patent No.: US 8,859,803 B2
(45) Date of Patent: Oct. 14, 2014

(54) PROCESS FOR PRODUCTION OF KETOMALONIC ACID COMPOUNDS OR HYDRATES THEREOF

(75) Inventor: Shinki Tani, Fuji (JP)

(73) Assignee: Ihara Chemical Industry Co., Ltd., Tokyo (JP)

(*) Notice: Subject to any disclaimer, the term of this patent is extended or adjusted under 35 U.S.C. 154(b) by 631 days.

(21) Appl. No.: 13/255,168

(22) PCT Filed: Jun. 25, 2010

(86) PCT No.: PCT/JP2010/004225
§ 371 (c)(1),
(2), (4) Date: Sep. 7, 2011

(87) PCT Pub. No.: WO2010/150548
PCT Pub. Date: Dec. 29, 2010

(65) Prior Publication Data
US 2012/0004443 A1 Jan. 5, 2012

(30) Foreign Application Priority Data
Jun. 26, 2009 (JP) ................................. 2009-152062

(51) Int. Cl.
C07C 67/313 (2006.01)
C07C 67/31 (2006.01)
C07C 69/716 (2006.01)
C07C 69/675 (2006.01)

(52) U.S. Cl.
CPC ............. C07C 69/716 (2013.01); C07C 69/675 (2013.01); C07C 67/31 (2013.01); C07C 67/313 (2013.01)
USPC ........................................................ 560/176

(58) Field of Classification Search
CPC .... C07C 67/313; C07C 67/31; C07C 69/716; C07C 69/675
USPC ........................................................ 560/176
See application file for complete search history.

(56) References Cited

U.S. PATENT DOCUMENTS

| 4,296,114 | A | 10/1981 | Appleton et al. |
| 4,584,145 | A | 4/1986 | Santi et al. |
| 6,329,389 | B1 | 12/2001 | Suzuki et al. |
| 6,348,461 | B1 | 2/2002 | Takano et al. |

FOREIGN PATENT DOCUMENTS

| DE | 3345268 A1 | 7/1984 |
| JP | 54-66696 A | 5/1979 |
| JP | 61-12647 A | 1/1986 |
| JP | 8-151346 A | 6/1996 |
| JP | 2002-201144 A | 7/2002 |
| WO | 2005/21547 A2 | 3/2005 |

OTHER PUBLICATIONS

Chen, Wenzheng et al., "A convenient partical method for the preparation of diethyl oxomalonate", Chemistry (Huaxue Tongbao), Year 1986, Issue 9, pp. 35, Russian Office Action dated Jan. 20, 2014, With English Translation, (5 pages).
Notification of Transmittal of Translation of the International Preliminary Report on Patentability (Form PCT/IB/338) of International Application No. PCT/JP2010/004225 mailed Jan. 26, 2012, with Forms PCT/IB/326, PCT/18373 and PCT/ISA/237.
Chen, Wuzheng et al., "A convenient practical method for the preparation of diethyl oxomalonate", Huaxue Tongbao, 1986.
Silvestre, Samuel M., "Allylic and benzylic oxidation reactions with sodium chlorite", Tetrahedron, 2007, vol. 63, 2439-2445 (7 pages).
Russian Office Action dated Jan. 20, 2014, issued in corresponding Russian Application No. 2012102669/04, w/ English translation (8 pages).
Chemical Abstracts, vol. 123, p. 256144, year—1994.
Liu et al., "Oxidation of $\alpha$-Methyl or $\alpha$-Methylene Groups in Carbonyl Compounds with Ammonium Chlorochromate", Chinese Chemical Letters, vol. 3, No. 8, pp. 585-588, 1992.
Clark-Lewis et al, "Quinoxaline Derivatives. Part IV.* Dihydro-oxo-1:4:5-triaza-naphthalenecarboxyureides and Related spiroHydantoins", J. Chem. Soc., 1957, pp. 430-439.
Garratt, "Diethyl Oxomalonate", e-EROS Encyclopedia of Reagents for Organic Synthesis, 3771 (2001), pp. 3711-3719.
Harayama et al., "Hydrolysis Products of Flavins (Isoalloxazines)", J. Chem. Soc., Perkin Tans, vol. 1, 1987, pp. 75-83.
International Search Report for PCT/JP2010/004225, dated Jul. 27, 2010.
Astin et al., "Selenium Dioxide, a New Oxidising Agent" Part III, J.C.S., 1933, pp. 391-394.
"Organic Syntheses", An Annual Publication of Satisfactory Methods for the Preparation of Organic Chemicals, vol. 71, 1993, pp. 214-219.
Dox, "Ethyl Oxomalonate", O.S., vol. 4,1925, pp. 27-28.
Saba, "Synthesis of Vicinal Trioxo Compounds by Dimethyl Dioxirane Oxidation of 2-Diazo-1-3-Dioxo Derivatives", Synthetic Communications, vol. 24, No. 5, pp. 695-699, 1994.

Primary Examiner — Yevegeny Valenrod
(74) Attorney, Agent, or Firm — Westerman, Hattori, Daniels & Adrian, LLP

(57) ABSTRACT

Disclosed is a process for the production of ketomalonic acid compounds or hydrates thereof by reacting a malonic acid compound with one or more chlorous acid compounds selected from among chlorous acid and chlorites and thus oxidizing the methylene group of the malonic acid compound. The process does not necessitate highly toxic reagents, lowly safe reagents, special reactants, special reaction equipment, expensive reagents, expensive catalysts, or transition metals such as noble metals, and permits the selection of mild reaction conditions and simple operation, thus enabling efficient and easy production of ketomalonic acid compounds such as ketomalonic diesters under simple and easy conditions suitable for industrialization.

12 Claims, No Drawings

PROCESS FOR PRODUCTION OF KETOMALONIC ACID COMPOUNDS OR HYDRATES THEREOF

TECHNICAL FIELD

The present invention relates to a method of producing a ketomalonic acid compound such as ketomalonic acid diester or a hydrate thereof far more effectively than that of the past, by reacting a malonic acid compound such as malonic acid diester with a chlorous acid compound.

BACKGROUND ART

A ketomalonic acid diester or a hydrate thereof is a compound useful as a raw material in production of a pyrazin-2-on-3-carboxylic acid ester derivative by reaction with diamine (see Patent Documents 1 to 4, and Non-patent Documents 1 to 2). This reaction is used in production of a medicine or an agricultural chemical, and the like, particularly as a method for producing a quinoxalinone derivative from aromatic diamine.

Conventionally, as a synthesis method of ketomalonic acid diester from malonic acid diester, direct methods and indirect methods were reported. However, none of them has been industrialized due to the toxicity or the difficulty in handling reagents, and the like. As a synthesis method of ketomalonic acid diester from malonic acid diester, known is, for example, a process of producing ketomalonic acid diester by oxidizing malonic acid diester with an oxidant such as selenium dioxide (for example, see Non-patent Document 3 wherein the yield rate is 32.3% of the theoretical yield on the basis of selenium dioxide used), dinitrogen trioxide (for example, see Non-patent Document 4 wherein the yield rate is 74 to 76%) and chromium trioxide (for example, see Non-patent Document 6 wherein the yield rate 70%). However, these methods have problems such as toxicity of reagents, poor safety or operability of reagents, low yield rate, use of a special reactor, or use of a transitional metal.

In addition, there are known methods of producing ketomalonic acid diester as follows: a method of reacting a compound in which the active methylene moiety of malonic acid diester is substituted with bromine, with silver nitrate (for example, see Non-patent Document 7), a method of reacting an azo group-substituted compound with dimethyl dioxirane (for example, see Non-patent Document 8), a method of reacting a methylene group-substituted compound with ozone (for example, see Non-patent Documents 5 and 9), a method of reacting a hydroxy group-substituted compound with a noble metal catalyst (for example, see Patent Document 5) and the like. However, these methods have drawbacks of using tartronic acid which is far more expensive than malonic acid diester, as a raw material, or necessity for previous modification of the active methylene moiety of malonic acid diester, or have economical and operational problems. In addition, these processes have problems such as use of expensive reagents, use of special reacting agents, use of special reactors, use of expensive catalysts, or use of transitional metals.

CITATION LIST

Patent Document

Patent Document 1: U.S. Pat. No. 6,329,389
Patent Document 2: U.S. Pat. No. 6,348,461
Patent Document 3: U.S. Pat. No. 4,296,114
Patent Document 4: WO 2005/21547
Patent Document 5: Japanese Patent Application Laid-Open (JP-A) No. 8-151346

Non-Patent Document

Non-Patent Document 1: J. W. Clark-Lewis, et al., J. Chem. Soc., 1957, 430-439.
Non-Patent Document 2: Fumio Yoneda, et al., J. Chem. Soc. Perkin Transactions 1, 1987, 75-83.
Non-Patent Document 3: S. Astin et al., J. Chem. Soc., 1933, 391-394.
Non-Patent Document 4: A. W. Dox, Organic Syntheses, 4, 1925, 27-28.
Non-Patent Document 5: Encyclopedia of Reagents for Organic Synthesis, 3711 (2001).
Non-Patent Document 6: Liang Xian liu et al., Chinese Chemical Letters, 3, 1992, 585-588.
Non-Patent Document 7: Chem. Abstr. 123: 256144.
Non-Patent Document 8: Antonio Saba, Synthetic Communications, 24, 695-699 (1994).
Non-Patent Document 9: Lutz F., et al., Organic Syntheses, 71, 214-219 (1993)

SUMMARY OF THE INVENTION

Problems to be Solved by the Invention

The object of the present invention is to provide a novel method of producing a ketomalonic acid compound such as ketomalonic acid diester, which resolves the drawbacks of the conventional arts described above.

Another object of the present invention is to provide a method of producing a ketomalonic acid compound such as ketomalonic acid diester, which does not necessitate a special reactor or a reacting agent, and is a new and simple method allowing industrialization under easy conditions.

Means for Solving the Problems

Under the above-mentioned circumstances, the present inventors conducted researches earnestly on a method of producing a ketomalonic acid compound such as ketomalonic acid diester effectively, and as results, found out that the methylene moiety of a malonic acid derivative is selectively oxidized by specifically reacting a malonic acid compound such as malonic acid diester with a chlorous acid compound to whereby to produce a corresponding keto body, and thus completed the present invention based on these findings.

Specifically, the present invention relates to a method of producing a ketomalonic acid compound or a hydrate thereof by reacting a malonic acid compound such as malonic acid diester with one or two or more chlorous acid compounds selected from a chlorous acid or a salt of chlorous acid to oxidize the active methylene group of the malonic acid compound to produce a corresponding ketomalonic acid compound or a hydrate thereof.

If the method of the present invention is represented by using chemical formulae, the present invention relates to a method of producing a ketomalonic acid compound represented by following general formula (2):

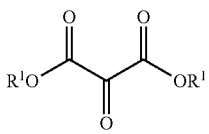

(2)

(wherein R[1] may be the same or different from each other and represents a hydrogen atom, an alkyl group which may be substituted with, a cyclic alkyl group which may be substituted with, an aromatic hydrocarbon group which may be substituted with, or an aromatic heterocyclic group which may be substituted with, and the two R[1]s may bind to each other to form a cyclic structure as a whole molecule) or a hydrate thereof, which is characterized by reacting a malonic acid compound represented by following general formula (1):

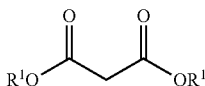

(1)

(wherein R[1] is the same as described above) or a mixture thereof (hereinafter, it may be simply described as the "raw material compound")

with one or two or more chlorous acid compounds selected from a chlorous acid or a salt of chlorous acid to oxidize the malonic acid compound.

In addition, the present invention relates to the above-mentioned production method wherein the reaction is conducted in the presence of an acid, particularly a carboxylic acid compound.

Effects of the Invention

According to the method of the present invention, provided is a method for industrial production of a ketomalonic acid compound such as ketomalonic acid diester. According to the method of the present invention, an active methylene site of a malonic acid compound such as malonic acid diester is oxidized, and at the time, a malonic acid compound such as malonic acid diester represented by a general formula (1), which is easily available, may be used as a raw material.

The method of the present invention can produce a ketomalonic acid compound such as ketomalonic acid diester without requiring any highly toxic reagents, any low safety reagents, any special reactants, any special reactors, any expensive reagents, any expensive catalysts, or any transition metals such as noble metals. The a malonic acid compound such as malonic acid diester as a raw material in the method of the present invention is a compound that is widely used in organic synthesis, and safe and easily available. Also, the salt of chlorous acid used as an oxidant is a substance used as a bleaching agent for pulp, fiber, or food, and as a disinfectant of tap water, and is a compound that is highly safe.

In addition, the method of the present invention can produce a ketomalonic acid compound such as ketomalonic acid diester, and does not necessitate previous modification of the active methylene moiety of malonic acid diester, allows direct reaction of a malonic acid derivative, and has no economical and operational problems.

The method of the present invention can produce a ketomalonic acid compound such as ketomalonic acid diester in high yield rate with high selectivity.

Furthermore, the method of the present invention can produce a ketomalonic acid compound such as ketomalonic acid diester allowing selection of mild reacting conditions in good operability under simple conditions suitable for industrialization.

In addition, the method of the present invention gives no harmful waste products derived from catalysts or transitional metals, and thus allows easy treatment for the waste products, and is environmentally friendly, and has high industrial use value.

MODES FOR CARRYING OUT THE INVENTION

Hereinafter, the present invention will be described.

If the present invention is described more specifically, the present inventions are as described below in [1] to [28].

[1] The method of producing a ketomalonic acid compound represented by following general formula (2):

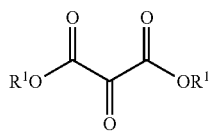

(2)

(wherein R[1] may be the same or different from each other and represents a hydrogen atom, an alkyl group which may be substituted with, a cyclic alkyl group which may be substituted with, an aromatic hydrocarbon group which may have a substituent, or an aromatic heterocyclic group which may have a substituent, and the two R[1]s may bind to each other to form a cyclic structure as a whole molecule) or a hydrate thereof, by reacting a malonic acid compound represented by following general formula (1):

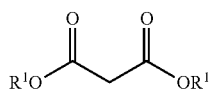

(1)

(wherein R[1] is the same as described above) or a mixture thereof (hereinafter, it may be simply described as the "raw material compound"), with one or two or more chlorous acid compounds selected from a chlorous acid or a salt of chlorous acid, to oxidize the methylene group of the above-mentioned malonic acid compound.

[2] The method of producing a ketomalonic acid compound or a hydrate thereof according to the above-mentioned [1], wherein the reaction of the malonic acid compound and the chlorous acid compound is conducted in the presence of an acid.

[3] The method of producing a ketomalonic acid compound or a hydrate thereof according to the above-mentioned [2], wherein the acid is a carboxylic acid compound.

[4] The method of producing a ketomalonic acid compound or a hydrate thereof according to the above-mentioned [3], wherein the carboxylic acid compound is one or two or more carboxylic acid compounds selected from the group consisting of a carboxylic acid, a salt of carboxylic acid, and an anhydride of carboxylic acid.

[5] The method of producing a ketomalonic acid compound or a hydrate thereof according to the above-mentioned

[3] or [4], wherein the carboxylic acid compound is a carboxylic acid or an anhydride of carboxylic acid.

[6] The method of producing a ketomalonic acid compound or a hydrate thereof according to any one of the above-mentioned [3] to [5], wherein the carboxylic acid compound is an acetic acid or an anhydrous acetic acid.

[7] The method of producing a ketomalonic acid compound or a hydrate thereof according to the above-mentioned [6], wherein the carboxylic acid compound is an acetic acid.

[8] The method of producing a ketomalonic acid compound or a hydrate thereof according to the above-mentioned [3] or [4], wherein the carboxylic acid compound is a combination of a carboxylic acid with a salt of carboxylic acid.

[9] The method of producing a ketomalonic acid compound or a hydrate thereof according to the above-mentioned [8], wherein the salt of carboxylic acid is an alkali metal salt of carboxylic acid or an alkali earth metal salt of carboxylic acid.

[10] The method of producing a ketomalonic acid compound or a hydrate thereof according to the above-mentioned [8] or [9], wherein the salt of carboxylic acid is an alkali metal salt of carboxylic acid.

[11] The method of producing a ketomalonic acid compound or a hydrate thereof according to any one of the above-mentioned [8] to [10], wherein the carboxylic acid compound is an acetic acid and a sodium acetate.

[12] The method of producing a ketomalonic acid compound or a hydrate thereof according to any one of the above-mentioned [1] to [11], wherein the reaction of the malonic acid compound with the chlorous acid compound is conducted in the presence of a solvent.

[13] The method of producing a ketomalonic acid compound or a hydrate thereof according to the above-mentioned [12], wherein the solvent is a polar solvent.

[14] The method of producing a ketomalonic acid compound or a hydrate thereof according to the above-mentioned [12] or [13], wherein the solvent is water, a carboxylic acid, nitriles, ketones, alcohols, esters, an acid anhydride, amides, sulfoxides, or sulfones.

[15] The method of producing a ketomalonic acid compound or a hydrate thereof according to any one of the above-mentioned [12] to [14], wherein the solvent is water, a carboxylic acid, nitriles, alcohols, esters, an acid anhydride, or amides.

[16] The method of producing a ketomalonic acid compound or a hydrate thereof according to any one of the above-mentioned [12] to [15], wherein the solvent is water, an acetic acid, acetonitrile, acetone, isobutylmethyl ketone, methanol or ethyl acetate.

[17] The method of producing a ketomalonic acid compound or a hydrate thereof according to any one of the above-mentioned [12] to [16], wherein the solvent is water, an acetic acid, acetonitrile, methanol or ethyl acetate.

[18] The method of producing a ketomalonic acid compound or a hydrate thereof according to any one of the above-mentioned [12] to [17], wherein the solvent is water or an acetic acid.

[19] The method of producing a ketomalonic acid compound or a hydrate thereof according to any one of the above-mentioned [12] to [18], wherein the solvent is water.

[20] The method of producing a ketomalonic acid compound or a hydrate thereof according to any one of the above-mentioned [12] to [19], wherein the reaction of the malonic acid compound with the chlorous acid compound is conducted in the presence of a hydrous solvent whereby to produce a hydrate of the ketomalonic acid compound.

[21] The method of producing a ketomalonic acid compound or a hydrate thereof according to above-mentioned [20], wherein the hydrate of the ketomalonic acid compound is subjected to heat treatment or dehydration treatment whereby to produce a ketomalonic acid compound.

[22] The method of producing a ketomalonic acid compound or a hydrate thereof according to any one of the above-mentioned [1] to [21], wherein the reaction of the malonic acid compound with the chlorous acid compound is conducted in a pH range of pH 2 to pH 7.

[23] The method of producing a ketomalonic acid compound or a hydrate thereof according to the above-mentioned [22], wherein the pH range is pH 4 to pH 7.

[24] The method of producing a ketomalonic acid compound or a hydrate thereof according to the above-mentioned [22] or [23], wherein the pH range is pH 4 to pH 6.

[25] The method of producing a ketomalonic acid compound or a hydrate thereof according to any one of the above-mentioned [1] to [24], wherein the chlorous acid compound is a salt of chlorous acid.

[26] The method of producing a ketomalonic acid compound or a hydrate thereof according to any one of the above-mentioned [1] to [25], wherein the chlorous acid compound is an alkali metal salt of chlorous acid or an alkali earth metal salt of chlorous acid.

[27] The method of producing a ketomalonic acid compound or a hydrate thereof according to any one of the above-mentioned [1] to [26], wherein the chlorous acid compound is an alkali metal salt of chlorous acid.

[28] The method of producing a ketomalonic acid compound or a hydrate thereof according to any one of the above-mentioned [1] to [27], wherein the chlorous acid compound is sodium chlorite.

A first feature of the present invention is reaction of a chlorous acid compound whereby to oxidize the compound represented by a general formula (1). The inventors found out that a chlorous acid compound has ability to specifically oxidize the methylene group of a malonic acid compound. For example, even though a hypochlorous acid compound, a bromous acid compound or the like, which is an similar oxidant to the oxidant of the present invention, i.e., a chlorous acid compound, is used, the intended reaction does not proceed. As described later, Comparative Example 1 describes an example wherein sodium hypochlorite is used, Comparative Example 2 describes an example wherein sodium chlorate is used, Comparative Example 3 describes an example wherein sodium perchlorate is used, and Comparative Example 4 describes an example wherein sodium bromite is used. However, in the examples where these oxidants were used, the intended diethyl ketomalonate could not be detected. It was not reported in the past that the methylene group of a malonic acid compound such as diethyl malonate could be oxidized with a halogen-based oxidant. In addition, the methylene group of a malonic acid compound was not oxidized with ordinary halogen-based oxidants as shown in Comparative Examples 1 to 4. However, surprisingly, it was found out for the first time that when a chlorous acid compound is used as an oxidant, the intended oxidation reaction proceeds, which is the present invention.

A second feature of the present invention is a combination of a salt of chlorous acid and a carboxylic acid as a chlorous acid compound. Free chlorous acid is very unstable, and is decomposed at room temperature by disproportional reaction. Consequently, ordinarily, a method of generating chlorous acid in a reaction system is performed by bringing a salt of chlorous acid such as barium chlorate and sodium chlorite into contact with an acid. For example, it is known to obtain an aqueous solution of free chlorous acid by bringing barium chlorite into contact with dilute sulfuric acid.

The present inventors further studied the acid to be used, and found out that a carboxylic acid such as an acetic acid is suitable as the acid. Details for action of the carboxylic are not sufficiently elucidated. However, as shown in Comparative Example 5 described below, it is presumed that when a mineral acid such as a hydrochloric acid is used, chlorous acid is generated too early, and thus the reaction with the malonic acid compound as a raw material is not sufficient. On the other hand, when the carboxylic acid of the present invention is used, the intended oxidation reaction proceeds in sufficient yield rate because it is presumed that the reaction moderately proceeds, and the reaction with the malonic acid compound as a raw material moderately proceeds.

A third feature of the present invention is that the reaction can be conducted in a hydrous solvent. Water is very safe, and inexpensive and easy to handle. Thus, a salt of chlorous acid used in the method of the present invention is well dissolved in water, and water can be used as a solvent. Furthermore, along with water, a water-miscible organic solvent, for example, a water-miscible organic solvent such as acetic acid, THF, methanol and DMF may be combined. Carboxylic acids such as acetic acid can be used not only as the above-mentioned carboxylic acid, but can be used as one of the solvents at the same time, and is one kind of preferable solvents in the method of the present invention.

A ketomalonic acid compound produced according to the method of the present invention is a compound having a keto group between ester groups, and is a keto compound having an electron attractive group at a position adjacent to the keto group, and similarly to chloral, form a hydrate of the ketomalonic acid compound represented by following general formula (3):

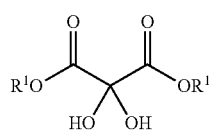

(wherein $R^1$ is the same as described above) in the presence of water. This hydrate may be subjected to heat treatment or dehydration treatment to form a ketomalonic acid compound of a keto type, and this compound becomes a hydrate in the presence of water. Such reversible reaction is similar to general properties of hydrates such as hydrous chloral.

By the method of producing a ketomalonic acid compound or a hydrate thereof according to the present invention, a hydrate of the ketomalonic acid compound can be isolated in production in the presence of water, for example, in a reaction using a hydrous solvent, or a ketomalonic acid compound of the keto type can be produced in an anhydrous system. In addition, as described above, the hydrate can be converted to a ketomalonic acid compound of the keto type if necessary.

The compound represented by a general formula (1) of the present invention as a raw material will be described. In the present specification, regarding the carbon number of substituents, for example, when the carbon number is 1 to 6, it may be briefly referred to as "$C_1$-$C_6$".

In the general formula (1), $R^1$ may be the same or different from each other and represents independently a hydrogen atom; a straight or branched $C_1$-$C_6$ alkyl group such as a methyl group, an ethyl group, a n-propyl group, an isopropyl group, a n-butyl group, a sec-butyl group, a t-butyl group, a n-pentyl group, and a n-hexyl group (the straight or branched alkyl group may have a substituent such as a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; an aryl group, for example, a phenyl group; and a heteroaryl group, for example, a pyridyl group or a furyl group); a cyclic $C_3$-$C_6$ alkyl group, for example, a cyclopropyl group, a cyclobutyl group, a cyclopentyl group or a cyclohexyl group (the cyclic alkyl group may have a substituent such as a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; an aryl group, for example, a phenyl group; and a heteroaryl group, for example, a pyridyl group or a furyl group); a phenyl group (the phenyl group may have a substituent such as a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; a halogen atom, for example, bromo, chloro, fluoro and iodo; an aryl group, for example, a phenyl group; and a heteroaryl group, for example, a pyridyl group or a furyl group); or a heteroaryl group such as a pyridyl group and a furanyl group (the heteroaryl group may have a substituent such as a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; a halogen atom, for example, bromo, chloro, fluoro and iodo; an aryl group, for example, a phenyl group; and a heteroaryl group, for example, a pyridyl group or a furyl group).

Examples of the malonic acid compound represented by the general formula (1) include specifically, for example, malonic acid, dimethyl malonate, diethyl malonate, di n-propyl malonate, diisopropyl malonate, di n-butyl malonate, diisobutyl malonate, di sec-butyl malonate, di t-butyl malonate, di n-pentyl malonate, di n-hexyl malonate, dicyclopropyl malonate, dicyclopentyl malonate, dicyclohexyl malonate, diphenyl malonate, di(4-pyridyl) malonate, di(2-pyridyl) malonate, methylethyl malonate, methyl n-propyl malonate, ethyl n-propyl malonate, methylphenyl malonate, methyl (4-pyridyl) malonate, methyl(2-pyridyl) malonate and the like. Examples of preferable malonic acid compound include malonic acid dialkyl esters, particularly diethyl malonate ester.

The malonic acid compound represented by the general formula (1) (raw material compound) is a known compound, or a compound that can be produced by an ordinary method, for example, esterification of malonic acid, and the like.

Next, the chlorous acid compound used in the method of the present invention will be described.

In the method of the present invention, one or two or more chlorous acid compounds selected from chlorous acid or a salt of chlorous acid are used.

The salt of chlorous acid is a salt forming cation with chlorous acid ion, but is not limited thereto.

Examples of the cation include a metal cation or an onium cation, but are not limited thereto.

Examples of the metal cation include an alkali metal ion such as a lithium ion, a sodium ion, a potassium ion or a cesium ion; an alkali earth metal ion such as a magnesium ion, a calcium ion or a barium ion; an earth metal ion such as aluminum; a zinc-family ion such as zinc; a transitional metal ion such as a copper ion, a silver ion, a nickel ion, a manganese ion or an iron ion, but are not limited thereto.

Examples of the onium cation include an ammonium ion ($NH_4^+$); a quaternary ammonium ion having a straight or branched $C_1$-$C_8$ alkyl group or a phenyl group such as a tetramethyl ammonium ion, a tetrabutyl ammonium ion, a tetraoctyl ammonium ion, a trimethylbutyl ammonium ion, a trimethyloctyl ammonium ion, a tributylmethyl ammonium ion or a trioctylmethyl ammonium ion; a quaternary phosphonium ion having a straight or branched $C_1$-$C_8$ alkyl group or a phenyl group such as a tetramethyl phosphonium ion, a tetrabutyl phosphonium ion or a tetraphenyl phosphonium ion, but are not limited thereto.

Furthermore, examples of the salt of chlorous acid also include a salt of chlorous acid and amines (amine salt).

Examples of the amines forming the salt include methyl amine, dimethyl amine, trimethyl amine, ethyl amine, diethyl amine, triethyl amine, propyl amine, dipropyl amine, tripropyl amine, butyl amine, dibutyl amine, tributyl amine, diisopropylethyl amine, hydrazine, methyl hydrazine, pyridine, 2-methylpyridine, 3-methylpyridine, 4-methylpyridine, 2,4-dimethylpyridine, quinoline, aniline, or N,N-diethyl aniline and the like, but are not limited thereto.

These salts of chlorous acid may be an anhydride or a hydrate.

These salts of chlorous acid may be a mono salt or a double salt.

Examples of the chlorous acid compound specifically include, for example, a chlorous acid; an alkali metal salt of chlorous acid including lithium chlorite, sodium chlorite, sodium chlorite trihydrate, or potassium chlorite and the like; an alkali earth metal salt of chlorous acid including magnesium chlorite, magnesium chlorite trihydrate, calcium chlorite, calcium chlorite trihydrate, barium chlorate, or barium chlorate dihydrate and the like; an earth metal salt of chlorous acid such as aluminum chlorite; a zinc-family salt of chlorous acid such as zinc chlorite dihydrate; a transitional metal salt of chlorous acid such as copper chlorite (II), copper chlorite (III), silver chlorite, nickel chlorite dihydrate or manganese chlorite; ammonium chlorite; a quaternary ammonium salt of chlorous acid such as ammonium tetramethyl chlorite; a quaternary phosphonium salt of chlorous acid such as phosphonium (2,4-dinitrophenyl) triethyl chlorite; an amine salt of chlorous acid such as a methyl amine salt of chlorous acid, a tripropyl amine salt of chlorous acid, a hydrazine salt of chlorous acid, a pyridine salt of chlorous acid, a 4-methyl pyridine salt of chlorous acid, a 2,4-dimethylpyridine salt of chlorous acid or a quinoline salt of chlorous acid; a double salt such as $KClO_2 \cdot NaClO_2$, $Cu(ClO_2)_2 \cdot 2KClO_2 \cdot 2H_2O$, $Cu(ClO_2)_2 \cdot Mg(ClO_2)_2 \cdot 8H_2O$, or $Cu(ClO_2)_2 \cdot Ba(ClO_2)_2 \cdot 4H_2O$ and the like, but are not limited thereto.

These chlorous acid compounds are known compounds.

These chlorous acid compounds may be used alone, or may be combined in 2 or more kinds in any ratio.

These chlorous acid compounds may be used in any form such as liquid or solid of the chlorous acid compound only, or an aqueous solution or a solution of solvent other than water. Examples of the solvent other than water include a solvent used in the reactions described below, but are not limited thereto.

The chlorous acid compound is preferably a salt of chlorous acid, more preferably an alkali metal salt of chlorous acid or an alkali earth metal salt of chlorous acid, further preferably an alkali metal salt of chlorous acid, further preferably sodium chlorite or potassium chlorite, and further preferably sodium chlorite from a viewpoint of availability, simplicity of handling, reactivity, and the like.

The molar ratio of the chlorous acid compound to be used in the reaction may be any molar ratio to the raw material compound represented by the general formula (1), at which the reaction proceeds. When the raw material compound is a compound represented by the general formula (1), the molar ratio of the chlorous acid compound is ordinarily, for example, in a range of 1.0-15.0 mol, preferably in a range of 1.5-5.0 mol, and more preferably in a range of 2.0-3.5 mol per 1 mol of the raw material compound.

The method of the present invention is preferably conducted under an acidic condition. The pH in the method of the present invention is preferably in a range of pH 2 to pH 7, more preferably in a range of pH 4 to pH 7, and further preferably in a range of pH 4 to pH 6. It is undesirable to lower pH extremely using a mineral acid such as hydrochloric acid (see Comparative Example 5).

In addition, in a preferable aspect of the present invention, the reaction is conducted in a buffer solution such as sodium acetate buffer solution to prevent the pH change during the reaction from increase.

Next, the carboxylic acid compound in the present invention will be described.

The method of the present invention is preferably conducted in the presence of a carboxylic acid compound, wherein the carboxylic acid compound is one kind or two or more kinds selected from the group consisting of a carboxylic acid, a salt of carboxylic acid, and an anhydride of carboxylic acid.

Examples of the carboxylic acid compound in the method of the present invention include an organic carboxylic acid such as an aliphatic carboxylic acid, an alicyclic carboxylic acid, an aromatic aliphatic carboxylic acid, an aromatic carboxylic acid and a heterocyclic carboxylic acid. Examples of preferable carboxylic acid include a carboxylic acid compound represented by the following general formula (4):

$$R^2COOH \tag{4}$$

(wherein $R^2$ may be the same or different from each other and represents a hydrogen atom, a alkyl group which may be substituted with, a cyclic alkyl group which may be substituted with, or a phenyl group which may have a substituent, or an aromatic heterocyclic group which may have a substituent).

$R^2$ in the general formula (4) may be the same or different from each other and represents independently a hydrogen atom; a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group (the straight or branched alkyl group may have a substituent such as a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; an aryl group, for example, a phenyl group; and a heteroaryl group, for example, a pyridyl group or a furyl group); a cyclic $C_3$-$C_6$ alkyl group, for example, a cyclopropyl group, a cyclobutyl group, a cyclopentyl group or a cyclohexyl group (the cyclic alkyl group may have a substituent such as a straight or branched $C_3$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; an aryl group, for example, a phenyl group; and a heteroaryl group, for example, a pyridyl group or a furyl group); a phenyl group (the phenyl group may have a substituent such as a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; a halogen atom, for example, bromo, chloro, fluoro and iodo; an aryl group, for example, a phenyl group; and a heteroaryl group, for example, a pyridyl group or a furyl group); and a heteroaryl group such as a pyridyl group and a furanyl group (the heteroaryl group may have a substituent such as a straight or branched $C_1$-$C_6$ alkyl group, for example, a methyl group, an ethyl group, a n-propyl group, an isopropyl group, a n-butyl group, a sec-butyl group, a t-butyl group, a n-pentyl group or a n-hexyl group; a cyclic $C_3$-$C_6$ alkyl group, for example, a cyclopropyl group, a cyclobutyl group, a cyclopentyl group or a cyclohexyl group; a hydroxyl group; a straight or branched $C_1$-$C_6$ alkoxy group, for example, a methoxy group, an ethoxy group, a n-propoxy group or an isopropoxy group; a halogen atom, for example, bromo, chloro, fluoro and iodo; an aryl group, for example, a phenyl group; and a heteroaryl group, for example, a pyridyl group or a furyl group).

Examples of the salt of the carboxylic acids in the method of the present invention include a salt of the above-mentioned carboxylic acid compound represented by the general formula (4). Examples of the metal atom in metal ion to form the salt include an alkali metal atom of a lithium atom, a sodium atom, or a potassium atom; an alkali earth metal atom such as a magnesium atom, a calcium atom, or a barium atom; an earth metal atom such as aluminum; a zinc-family atom such as zinc; a transitional metal atom such as a copper atom, a silver atom, a nickel atom, a lead atom, a manganese atom, or an iron atom, but are not limited thereto.

In addition, examples of the onium cation to form the salt include an ammonium ion ($NH_4^+$); a quaternary ammonium ion having a straight or branched $C_1$-$C_8$ alkyl group or a phenyl group such as a tetramethyl ammonium ion, a tetrabutyl ammonium ion, a tetraoctyl ammonium ion, a trimethylbutyl ammonium ion, a trimethyloctyl ammonium ion, a tributylmethyl ammonium ion and a trioctylmethyl ammonium ion; a quaternary phosphonium ion having a straight or branched $C_1$-$C_8$ alkyl group or a phenyl group such as a tetramethyl phosphonium ion, a tetrabutyl phosphonium ion and a tetraphenyl phosphonium ion, but are not limited thereto.

Furthermore, examples of the salt of carboxylic acid include a salt of a carboxylic acid with amines (amine salt of carboxylic acid).

Examples of the amines forming the salt of carboxylic acid include methyl amine, dimethyl amine, trimethyl amine, ethyl amine, diethyl amine, triethyl amine, propyl amine, dipropyl amine, tripropyl amine, butyl amine, dibutyl amine, tributyl amine, diisopropylethyl amine, pyridine, quinoline, isoquinoline, aniline, or N,N-diethyl aniline and the like, but are not limited thereto.

Examples of the anhydride of carboxylic acid in the method of the present invention include an anhydride of the above-mentioned carboxylic acid compound represented by the general formula (4). The anhydride of carboxylic acid may be formed from identical carboxylic acids only, or may be formed from different carboxylic acids. Such anhydride of carboxylic acid, which produces free carboxylic acid in water or a hydrous solvent system, is preferred.

In the method of the present invention, examples of the one or two or more carboxylic acid compounds selected from the group consisting of a carboxylic acid, a salt of carboxylic acid, and an anhydride of carboxylic acid, and specifically include, for example, a carboxylic acid such as an acetic acid and a propionic acid; an alkali metal salt of carboxylic acid such as sodium acetate, sodium propionate, potassium acetate and potassium propionate; an alkali earth metal salt of carboxylic acid such as magnesium acetate, magnesium propionate, calcium acetate and calcium propionate; a quaternary ammonium salt of carboxylic acid such as ammonium acetate, ammonium propionate and ammonium tetrabutyl acetate; a quaternary phosphonium salt of carboxylic acid such as phosphonium tetrabutyl acetate; an amine salt of carboxylic acid such as a triethyl amine salt of acetic acid, and a pyridine salt of acetic acid; an anhydride of carboxylic acid such as an anhydrous acetic acid and an anhydrous propionic acid, but are not limited thereto.

In the method of the present invention, the carboxylic acid compound selected from the group consisting of a carboxylic acid, a salt of a carboxylic acid and an anhydride of carboxylic acid, may be used alone, or may be used in combination of different 2 or more of any carboxylic acid compounds in any ratio.

When the carboxylic acid compound is used alone, the carboxylic acid compound is preferably, for example, a carboxylic acid or an anhydride of carboxylic acid, more preferably, for example, a carboxylic acid, and further preferably, for example, an aliphatic carboxylic acid such as an acetic acid or an aliphatic anhydride of carboxylic acid such as an anhydrous acetic acid, and particularly preferably an aliphatic carboxylic acid such as an acetic acid, but are not limited thereto.

When different 2 or more kinds of the carboxylic acid compounds are used in combination, the combination of the carboxylic acid compounds is preferably, for example, a combination of a carboxylic acid and a salt of carboxylic acid, more preferably, for example, a combination of a carboxylic acid and an alkali metal salt of carboxylic acid, and further preferably, for example, a combination of an aliphatic carboxylic acid and a salt thereof such as a combination of acetic acid and sodium acetate, but are not limited thereto.

The amount of the carboxylic acid compound used in the reaction may be any amount as long as the reaction sufficiently proceeds, but is, for example, in a range of 0.01-50 mole, preferably in a range of 0.2-10 mole, and more preferably in a range of 0.4-10 mole, per 1 mol of the malonic acid compound represented by the general formula (1). When a carboxylic acid is used as the carboxylic acid compound, the carboxylic acid may be used in large excess amount so as to also work as a solvent described below.

The method of the present invention may be implemented in the absence of a solvent, or may be implemented in the presence of a solvent.

As a solvent in the method of the present invention, the method of the present invention may be implemented in, for example, a solvent of water. When the chlorous acid compound is used as an aqueous solution, the method of the present invention may be sufficiently conducted with only a solvent of water derived from an aqueous solution of the chlorous acid compound. Furthermore, the method of the present invention may be conducted using a solvent other than water. A solvent that can be used in the reaction may be any solvent as long as it does not inhibit the reaction. For example, examples of the solvent include a carboxylic acid such as an acetic acid and a propionic acid; an acid anhydride such as an anhydrous acetic acid and an anhydrous propionic acid; nitriles such as acetonitrile and propionitrile; alcohols such as methanol, ethanol and ethylene glycol; esters represented by acetic acid ester such as methyl acetate, ethyl acetate and butyl acetate; ketones such as acetone, ethylmethyl ketone and isobutylmethyl ketone; amides such as dimethylformamide, dimethyl acetoamide and N-methylpyrolidone; alkyl ureas such as tetramethyl urea, phosphoric acid amides such as hexamethyl phosphoric triamide (HMPA), sulfoxides such as dimethyl sulfoxide; sulfones such as sulfolane or dimethyl sulfone; carbonic acid esters such as propylene carbonate; ether solvents such as diethyl ether and tetrahydrofuran, dioxane and the like. Furthermore, examples of the solvent include aromatic hydrocarbons such as toluene, xylene and chlorobenzene; halogenated aliphatic hydrocarbons such as dichloromethane and chloroform; aliphatic hydrocarbons such as pentane and n-hexane, and the like, but are not limited thereto. These solvents may be used alone, or may be used as a mixing solvent in any mixing ratio.

The solvent is preferably a polar solvent from a viewpoint of affinity and reactivity of the raw material compound with the chlorous acid compound, and the like. Furthermore, the solvent is preferably water, a carboxylic acid, nitriles, ketones, alcohols, esters, an acid anhydride, amides, sulfoxides, or sulfones. Furthermore, the solvent is preferably water, a carboxylic acid, nitriles, alcohols, esters, an acid anhydride, or amides. Furthermore, the solvent is preferably water, a carboxylic acid, nitriles, or alcohols. Furthermore, the solvent is preferably water, a carboxylic acid, or nitriles. Furthermore, the solvent is preferably water, an acetic acid, acetonitrile, acetone, isobutylmethyl ketone, methanol or ethyl acetate. Furthermore, the solvent is preferably water, an acetic acid, acetonitrile, methanol or ethyl acetate. Furthermore, the solvent is preferably water, an acetic acid, or acetonitrile. Furthermore, the solvent is preferably water or an acetic acid. Furthermore, the solvent is preferably water, which is simple and inexpensive.

Herein, the polar solvent is a solvent having a specific permittivity of 5 or more. Herein, the specific permittivity is a value described in The Chemical Society of Japan, "Handbook for Chemicals" (basics), 5$^{th}$ revision, pp. I-770-777, Maruzen Co., Ltd., 2004. The solvent used in the reaction is preferably a polar solvent having a specific permittivity of 5 or more, more preferably a polar solvent having a specific permittivity of 7 or more, further preferably a polar solvent having a specific permittivity of 17 or more, and particularly preferably a polar solvent having a specific permittivity of 20 or more.

If the polarity of the solvent remains too low, the reaction system becomes a bilayer, and thus the affinity reduces between the oily phase containing the raw material compound and the water phase containing the chlorous acid compound, whereby the reaction may hardly proceed, which is undesirable. However, without being limited thereto, the reaction may be implemented in the presence of any solvent.

As for the solvent, the reaction is preferably conducted in the presence of water solvent since a takeout form of the intended substance can be selected between a form of the ketomalonic acid compound represented by the general formula (2), or a form of a hydrate of the ketomalonic acid compound represented by the general formula (3) by suitable selection of treatment conditions in the post-reaction treatment.

The amount of the solvent may be any amount as long as it allows sufficient stirring of the reaction system, but is ordinarily in a range of 0.05 to 100 mole, and preferably 0.5 to 35 mol per 1 mol of the raw material compound represented by the general formula (1).

The reaction temperature of the reaction is, for example, in a range of 0° C. to the reflux temperature of the solvent to be used, preferably in a range of 0° C. to 60° C., and more preferably in a range of 5° C. to 30° C.

The reaction time of the reaction is not particularly limited, but preferably 0.5 hour to 24 hours, and more preferably 1 hour to 10 hours from a viewpoint of suppression of byproducts, and the like.

The reaction is an oxidation reaction, and, for example, if there is concern of heat generation involved with the reaction in big scale work, the heat generation involved with the reaction is preferably suppressed by adopting a suitable procedure such as proportional input or dropping input of a raw material.

Generally, if the reaction is implemented in the presence of water solvent, the product is obtained in a form of a hydrate of a ketomalonic acid compound represented by the general formula (3), and if the reaction is implemented under non-aqueous conditions, the product is obtained in a form of a ketomalonic acid compound represented by the general formula (2). In addition, if the reaction is implemented in the presence of water, and a product in a form of a ketomalonic acid compound represented by the general formula (2) is desired to be taken out, a hydrate of a ketomalonic acid compound represented by the general formula (3) may be dehydrated by conducting dehydration treatment such as toluene-azeotropic dehydration in the treatment after the reaction, to easily obtain a product in a form of a ketomalonic acid compound represented by the general formula (2). In other words, in the method of the present invention, the takeout form of the product can be made to any desired form between a form of a hydrate of a ketomalonic acid compound represented by the general formula (3) and a form of a ketomalonic acid compound represented by the general formula (2), by suitable selection in the reaction solvent or the post-reaction treatment.

Next, a method of producing the present invention compound will be specifically described by Examples, but the present invention is not limited to these Examples.

Herein, pH in each Example was measured by a hydrogen ion concentration indicator of glass electrode type, model: HM-20P manufactured by DKK-TOA CORPORATION.

Example 1

Production of Diethyl Ketomalonate

To a 1000 mL four-necked flask equipped with a mechanical stirrer, a dropping funnel and a thermometer, 496.8 g (1.37 mole) of 25% sodium chlorite aqueous solution, and then 26 mL (0.46 mole) acetic acid were slowly added. The pH in the reaction system was pH 4.4. Furthermore, 100 g (0.62 mole) of diethyl malonate was slowly added under room temperature, and then the mixture was stirred under room temperature for 3 hours, and then 490 mL ethyl acetate was added to the reaction system to separate the liquids. The organic layer was separated, and ethyl acetate was distilled off under reduced pressure. Toluene was added thereto to perform azeotropic dehydration and the toluene was distilled off under reduced pressure, to give 105 g of diethyl ketomalonate as an oily substance (97 yield rate).

$^1$H-NMR (300 MHz, CDCl$_3$) δ:
 4.41 (q, J=7.2 Hz, 2H), 1.40 (t, J=7.2 Hz, 3H) ppm.
$^{13}$C-NMR (300 MHz, CDCl$_3$) δ:
 178.2, 160.3, 63.6, 14.1 ppm.
GC-MS M$^+$=174.

Example 2

Production of a Hydrate of Diethyl Ketomalonate

To a 100 mL four-necked flask equipped with a mechanical stirrer, a dropping funnel and a thermometer, 49.6 g (0.137 mole) of 25% sodium chlorite aqueous solution, and then 2.6 mL (0.046 mole) of acetic acid were slowly added. The pH in the reaction system was pH 4.4. Furthermore, 10 g (0.062 mole) diethyl malonate was slowly added under room temperature, and then the mixture was stirred under room temperature for 3 hours, and then 49 mL ethyl acetate was added to the reaction system to separate the liquids. The organic layer was separated, and ethyl acetate was distilled off under reduced pressure, to give 11.6 g of diethyl ketomalonate hydrate (melting point: 54.6 to 56.9° C.) (97% yield rate).

$^1$H-NMR (300 MHz, CDCl$_3$) δ:
 4.31 (q, J=7.2 Hz, 2H), 1.30 (t, J=7.2 Hz, 3H) ppm.
$^{13}$C-NMR (300 MHz, CDCl$_3$) δ:
 168.6, 90.4, 63.7, 14.1 ppm.

Examples 3-7

To a 50 mL eggplant-shaped flask equipped with a magnetic stirrer, diethyl malonate (DEM), sodium chlorite (Na chlorite), acetic acid, sodium acetate (Na acetate), and water were put in the reaction scale and the molar ratio as shown in following Table 1. Herein, results of pH measurement in the reaction system are shown in Table 1. Furthermore, the mixture was stirred under room temperature for the time shown in Table 1, and then analyzed by gas chromatography (GC) to calculate the yield rate. The results are shown in Table 1.

TABLE 1

| Ex. No. | Reaction scale (DEM addition amount) mmol | Molar ratio(DEM = 1) | | | Water L/mol | pH — | Time hr | Yield GC area percent % |
|---|---|---|---|---|---|---|---|---|
| | | Na chlorite | Acetic acid | Na acetate | | | | |
| 3 | 5.19 | 2.20 | 0.48 | 0.10 | 1.0 | 5.3 | 7 | 100 |
| 4 | 5.62 | 2.20 | 0.44 | 0.13 | 1.0 | 5.5 | 8 | 100 |
| 5 | 6.06 | 2.20 | 0.41 | 0.17 | 1.0 | 5.8 | 24 | 100 |
| 6 | 5.19 | 2.20 | 0.48 | 0.10 | 2.0 | 5.2 | 24 | 100 |
| 7 | 5.19 | 2.20 | 0.48 | 0.10 | 3.0 | 5.2 | 24 | 100 |

As shown in Table 1, it is understood that the reaction proceeds nearly quantitatively by oxidation with chlorous acid.

Example 8

A reaction was performed similarly to Example 1 using 0.25 g (0.0016 mole) diethyl malonate, 0.95 mL (0.0166 mole) acetic acid, 1.71 g (0.0047 mole) of 25% sodium chlorite aqueous solution, and GC analysis was performed to give 88.1% GC total area value of diethyl ketomalonate.

Comparative Example 1

A reaction was performed similarly to Example 1 using 0.25 g (0.0016 mole) diethyl malonate and 0.94 mL (0.0164 mole) acetic acid, except that 8.14 g (0.0056 mole) of 5% sodium hypochlorite aqueous solution was used instead of 25% sodium chlorite aqueous solution. However, diethyl ketomalonate was not detected in GC analysis.

Comparative Example 2

A reaction was performed similarly to Example 1 using 0.25 g (0.0016 mole) diethyl malonate and 0.94 mL (0.0164 mole) acetic acid, except that 0.58 g (0.0056 mole) sodium chlorate was used instead of 25% sodium chlorite aqueous solution, and 1.49 mL water. However, diethyl ketomalonate was not detected in GC analysis.

Comparative Example 3

A reaction was performed similarly to Example 1 using 0.25 g (0.0016 mole) diethyl malonate and 0.94 ml (0.0164 mole) acetic acid, except that 0.67 g (0.0056 mole) sodium perchlorate was used instead of 25% sodium chlorite aqueous solution, and 1.49 mL water. However, diethyl ketomalonate was not detected in GC analysis.

Comparative Example 4

A reaction was performed similarly to Example 1 using 0.25 g (0.0016 mole) diethyl malonate and 0.94 mL (0.0164 mole) acetic acid, except that 0.74 g (0.0056 mole) sodium bromite was used instead of 25% sodium chlorite aqueous solution, and 1.49 mL water. However, diethyl ketomalonate was not detected in GC analysis, and dibromide was produced in 19.5%.

Comparative Example 5

A reaction was performed similarly to Example 1 using 0.25 g (0.0016 mole) diethyl malonate and 0.49 g (0.0056 mole) sodium chlorite, except that 0.48 mL (0.0056 mole) 35% hydrochloric acid was used instead of acetic acid and the pH at the time of the reaction initiation was 0.8. However, diethyl ketomalonate was not detected in GC analysis.

INDUSTRIAL APPLICABILITY

The method of the present invention can produce a ketomalonic acid diester represented by a general formula (2) or a hydrate thereof without requiring any highly toxic reagents, any low safety reagents, any special reactants, any special reactors, any expensive reagents, any expensive catalysts, or any transition metals such as noble metals.

Furthermore, according to the method of the present invention, it is possible to produce a ketomalonic acid diester represented by a general formula (2) or a hydrate thereof without previous modification of an active methylene moiety of malonic acid diester and without economical and operational problems.

Furthermore, according to the method of the present invention, it is possible to produce a ketomalonic acid diester represented by a general formula (2) or a hydrate thereof in high yield rate.

Furthermore, according to the method of the present invention, it is possible to produce a ketomalonic acid diester represented by a general formula (2) or a hydrate thereof in good operability, under easy conditions, suitable for industrial, under simple conditions.

The ketomalonic acid diester represented by the general formula (2) or a hydrate thereof obtained by the method of the present invention is a useful compound as an intermediate for a medicine or agricultural chemicals.

The invention claimed is:

1. A method of producing a ketomalonic acid compound represented by following general formula (2):

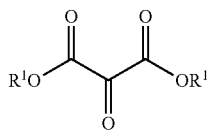

(wherein $R^1$ may be the same or different from each other and represents a hydrogen atom, an alkyl group which may be substituted with, a cyclic alkyl group which may be substituted with, an aromatic hydrocarbon group which may have a substituent, or an aromatic heterocyclic group which may have a substituent, and the two $R^1$s may bind to each other to form a cyclic structure as a whole molecule) or a hydrate thereof, by reacting a malonic acid compound represented by following general formula (1):

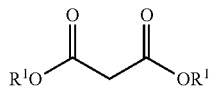

(wherein $R^1$ is the same as described above) or a mixture thereof, with one or two or more chlorous acid compounds selected from a chlorous acid or a salt of chlorous acid, to oxidize the malonic acid compound.

2. The method of producing a ketomalonic acid compound or a hydrate thereof according to claim 1, wherein the chlorous acid compound is a salt of chlorous acid.

3. The method of producing a ketomalonic acid compound or a hydrate thereof according to claim 1, wherein the chlorous acid compound is an alkali metal salt of chlorous acid or an alkali earth metal salt of chlorous acid.

4. The method of producing a ketomalonic acid compound or a hydrate thereof according to claim 1, wherein the chlorous acid compound is sodium chlorite.

5. The method of producing a ketomalonic acid compound or a hydrate thereof according to claim 1, wherein the reaction of a malonic acid compound or a mixture thereof with a chlorous acid compound is conducted in a range of pH 2 to pH 7.

6. The method of producing a ketomalonic acid compound or a hydrate thereof according to claim 1, wherein the reaction of a malonic acid compound or a mixture thereof with a chlorous acid compound is conducted in the presence of one or two or more carboxylic acid compounds selected from the group consisting of a carboxylic acid, a salt of carboxylic acid, and an anhydride of carboxylic acid.

7. The method of producing a ketomalonic acid compound or a hydrate thereof according to claim 6, wherein the carboxylic acid compound is a carboxylic acid.

8. The method of producing a ketomalonic acid compound or a hydrate thereof according to claim 6, wherein the carboxylic acid compound is an acetic acid.

9. The method of producing a ketomalonic acid compound or a hydrate thereof according to claim 6, wherein the carboxylic acid compound is a combination of a carboxylic acid with a salt of carboxylic acid.

10. The method of producing a ketomalonic acid compound or a hydrate thereof according to claim 6, wherein the carboxylic acid compound is a combination of a carboxylic acid with an alkali metal salt of carboxylic acid.

11. The method of producing a ketomalonic acid compound or a hydrate thereof according to claim 1, wherein the reaction of a malonic acid compound or a mixture thereof with a chlorous acid compound is conducted in the presence of a solvent.

12. The method of producing a ketomalonic acid compound or a hydrate thereof according to claim 11, wherein the solvent is a polar solvent.

* * * * *